United States Patent
Kettle et al.

(10) Patent No.: US 6,737,435 B1
(45) Date of Patent: May 18, 2004

(54) INDOLE DERIVATIVES AND THEIR USE AS MCP-1 ANTAGONIST

(75) Inventors: Jason G Kettle, Macclesfield (GB); Alan W Faull, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/889,599

(22) PCT Filed: Jan. 31, 2000

(86) PCT No.: PCT/GB00/00265

§ 371 (c)(1),
(2), (4) Date: Oct. 19, 2001

(87) PCT Pub. No.: WO00/46196

PCT Pub. Date: Aug. 10, 2000

(30) Foreign Application Priority Data

Feb. 5, 1999 (GB) ............................................. 9902461

(51) Int. Cl.$^7$ ...................... A61K 31/405; A61K 31/40; C07D 401/00; C07D 209/36; C07D 209/04
(52) U.S. Cl. .................... 514/415; 514/414; 546/276.4; 546/278.4; 548/484; 548/490
(58) Field of Search ................................. 514/414, 415; 548/484, 490; 546/276.4, 278.4

(56) References Cited

U.S. PATENT DOCUMENTS

| | | |
|---|---|---|
| 3,557,142 A | 1/1971 | Bell |
| 3,776,923 A | 12/1973 | Remers et al. |
| 3,997,557 A | 12/1976 | Helsley et al. |
| 4,529,724 A | 7/1985 | Ho |
| 4,608,384 A | 8/1986 | Wierzbicki et al. |
| 4,721,725 A | 1/1988 | Biller et al. |
| 4,751,231 A | 6/1988 | Halczenko et al. |
| 4,965,369 A | 10/1990 | Maetzel et al. |
| 5,081,145 A | 1/1992 | Guindon et al. ............ 514/419 |
| 5,190,968 A | 3/1993 | Gillard et al. |
| 5,254,563 A | 10/1993 | Huth et al. |
| 5,272,145 A | 12/1993 | Prasit et al. |
| 5,273,980 A | 12/1993 | Frenette et al. |
| 5,288,743 A | 2/1994 | Brooks et al. |
| 5,290,798 A | 3/1994 | Gillard et al. |
| 5,308,850 A | 5/1994 | Gillard et al. |
| 5,389,650 A | 2/1995 | Frenette et al. |
| 5,399,699 A | 3/1995 | Kolasa et al. |
| 5,482,960 A | 1/1996 | Berryman et al. |
| 5,684,032 A | 11/1997 | Elliott et al. |
| 5,852,046 A | 12/1998 | Lang et al. |
| 5,955,492 A | 9/1999 | Thompson et al. |
| 6,184,235 B1 | 2/2001 | Connor et al. |
| 6,288,103 B1 | 9/2001 | Faull et al. |
| 6,291,507 B1 | 9/2001 | Faull et al. |
| 6,441,004 B1 | 8/2002 | Faull et al. |
| 6,479,527 B1 | 11/2002 | Barker et al. |

FOREIGN PATENT DOCUMENTS

| | | |
|---|---|---|
| DE | 298 913 A5 | 3/1992 |
| EP | 0 077 209 | 7/1984 |
| EP | 0 114 014 | 7/1984 |
| EP | 0 186 367 | 7/1986 |
| EP | 0 189 690 | 8/1986 |
| EP | 0 419 049 A1 | 3/1991 |
| EP | 0 480 659 A2 | 4/1992 |

(List continued on next page.)

OTHER PUBLICATIONS

U.S. patent application Ser. No. 09/889,494, Faull et al., filed Jul. 18, 2001, WO 00/46198, Aug. 10, 2000.
U.S. patent application Ser. No. 09/889,493, Faull et al., filed Jul. 2, 2001, WO 00/46197, Aug. 10, 2000.
U.S. patent application Ser. No. 09/889,516, Faull et al., filed Oct. 2, 2001, WO 00/46199, Aug. 10, 2000.
U.S. patent application Ser. No. 09/889,515, Faull et al., filed Jul. 18, 2001, WO 00/46195, Aug. 10, 2000.
U.S. patent application Ser. No. 08/485,061, Faull et al., filed Feb. 3, 2000, WO 99/07351*, Feb. 18, 1999.
U.S. patent application Ser. No. 10/194,969, Faull et al., filed Jul. 15, 2002, WO 99/07351*, Feb. 18, 1999.
U.S. patent application Ser. No. 09/485,107, Faull et al., filed Feb. 3, 2000, WO 99/07678*, Feb. 18, 1999.
U.S. patent application Ser. No. 09/626,241, Faull et al., filed Jul. 26, 2000, WO 99/40913, Aug. 19, 1999.
U.S. patent application Ser. No. 09/626,378, Barker et al., filed Jul. 26, 2000, WO 99/40914, Aug. 19, 1999, WO 01/51467, Jul. 19, 2001.
U.S. patent application Ser. No. 10/169,717, Faull et al., filed Jul. 9, 2002, WO 01/51466, Jul. 19, 2001.
Berman et al., "Localization of Monocyte Chemoattractant Peptide–1 . . . Autoimmune Encephalomyelitis and Trauma in the Rat", Journal of Immunology, 1996, vol. 156, pp. 3017–3023; XP002105551 cited in the application, see the whole document.
Bobošik et al., "Synthesis of N–Phenylsulfonyl Protected Furo[3,2–b]pyrroles", Collect. Czech. Chem. Commun., vol. 59, 1994, pp. 499–205.

(List continued on next page.)

*Primary Examiner*—Ceila Chang
*Assistant Examiner*—Binta Robinson
(74) *Attorney, Agent, or Firm*—Morgan, Lewis & Bockius LLP

(57) ABSTRACT

A compound of formula (1) wherein R1 is hydrogen, halo or methoxy, R2 is hydrogen, halo, methyl, ethyl or methoxy; R3 is carboxy, tetrazolyl, or —CONHSO$_2$R$^4$ where R$^4$ is methyl, ethyl, phenyl, 2,5-dimethylisoxazolyl or trifluoromethyl; T is —CH$_2$— or —SO$_2$—; and ring A is 3-chlorophenyl, 4-chlorophenyl, 3-trifluoromethylphenyl, 3,4-dichlorophenyl, 3,4-difluorophenyl, 3-fluoro-4-chlorophenyl, 3-chloro-4-fluorophenyl or 2,3-dichloropyrid-5-yl; or a pharmaceutically acceptable salt or prodrug thereof, as well as pharmaceutical compositions containing them are described and claimed. These compounds and compositions are useful in the treatment of disease mediated by monocyte chemoattractant protein-1 or RANTES (Regulated Upon Activation, Normal T-cell Expressed and Secreted), such as inflammatory disease.

9 Claims, No Drawings

FOREIGN PATENT DOCUMENTS

| | | |
|---|---|---|
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 639 573 A1 | 2/1995 |
| EP | 0 822 185 A1 | 2/1998 |
| EP | 0 275 667 | 7/1998 |
| FR | 2 565 981 | 12/1985 |
| WO | WO 86/00896 | 2/1986 |
| WO | WO 93/12780 | 7/1993 |
| WO | WO 93/16069 | 8/1993 |
| WO | WO 93/20078 | 10/1993 |
| WO | WO 93/25546 | 12/1993 |
| WO | WO 94/14434 | 7/1994 |
| WO | WO 96/03377 | 2/1996 |
| WO | WO 96/18393 | 6/1996 |
| WO | WO 96/31492 | 10/1996 |
| WO | WO 96/33171 | 10/1996 |
| WO | WO 96/37467 | 11/1996 |
| WO | WO 96/37469 | 11/1996 |
| WO | WO 97/12613 | 4/1997 |
| WO | WO 97/12615 | 4/1997 |
| WO | WO 97/30704 | 8/1997 |
| WO | WO 97/35572 | 10/1997 |
| WO | WO 98/06703 | 2/1998 |
| WO | WO 99 07351 | 2/1999 |
| WO | WO 99/07678 | 2/1999 |
| WO | WO99/33800 * | 7/1999 |
| WO | WO 99/40913 | 8/1999 |
| WO | WO 99/40914 | 8/1999 |
| WO | WO 99/07678 | 9/1999 |
| WO | W0 00/46195 | 8/2000 |
| WO | WO 00/46196 | 8/2000 |
| WO | W0 00/46197 | 8/2000 |
| WO | WO 00/46198 | 8/2000 |
| WO | W0 00/46199 | 8/2000 |
| WO | W0 01/51466 | 7/2001 |
| WO | WO 01/51467 | 7/2001 |

OTHER PUBLICATIONS

Kataoka et al., Chemical Abstracts, vol. 123, No. 14, Oct. 2, 1995 Columbus, Ohio, US; abstract No. 179521d, Homopiperazines as cell migration inhibitors. Xp002081582 see abstract & JP 95 145060 A (TEJIN LTD).

Dandárová et al., "Reference Data", Magnetic Resonance in Chemistry, vol. 28, 1990, pp. 830–831.

Korobchenko et al., Database Chemabs, Chemical Abstracts Service, Columbus, Ohio, US, AN: 119:62465, XP002105556, see abstract & "Synthesis and antiviral activity of pyrrolecarboxylic acids and their derivatives" KHIM.–FARM.ZH., vol. 26, No. 11–12, 1992, pp. 57–59, see the whole document.

Elliott et al., Database Chemabs, Chemjical Abstracts Service, Columbus, Ohio, US, STN, accession No. 125:142551, XP002094570, see abstract. RN 179526–39–7.

Deleuran et al., "Localization of monocyte chemotactic and activating factor (MCAF/MCP–1) in psoriasis", Journal of Dermatological Science, 1996, vol. 13(3), pp. 228–236; XP002105554 cited in the application, see the whole doucment.

Derwent Abstract for JP 63284177 including Chemical Abstract Registry Records for specific compounds indexed.

Derwent and Chemical Abstracts for International Patent Application, Publication No. WO 92/04343.

Derwent World Patents Index record, JAPIO record and Chemical Abstract for Molecules (1997), 2(4), 69–79, including Chemical Abstract Registry records for specific compounds indexed.

Grimm et al., "Enhanced expression and production of monocyte chemoattractant protein–1 in inflammatory bowel disease mucosa", Journal of Leukocyte Biology, 1996, vol. 59(6) pp. 804–812; XP002105555 cited in the application, see the whole document.

Harrison et al.; "Cyclopenta[b]indoles, Part 2.[1] Model studies towards tremorgenic mycotoxins"; Journal of Chemical Society; 1995, pp. 1131–1136; XP002105550 cited in the application, see p. 1132, Scheme 3, compound 9.

Hartman et al., "The Synthesis of 5–alkylaminomethylthieno[2,3–b]pyrrole–5–sulfonamides", Heterocycles, vol. 29, 1989, pp. 1943–1949.

Satoshi et al., Japanese Abstract N–Phenylsulfonylindole derivatives, JP 04273857 A2.

Jones et al., "Potential Role of Monocyte Chemoattractant Protein 1/JE in . . . Alveolitis in the Rat", Journal of Immunology, 1992, vol. 149(6), pp. 2147–2154; XP002105552 cited in the application, see the whole document.

Koch et al., Enhanced Production of Monocyte Chemoattractant Protein –1 in Rheumatoid Arthritis, Journal of Clinical Investigation, 1992, vol. 90(3), pp. 772–779; XP002105553, cited in the application, see the whole document.

Krutosikova et al., "Condensed O–, N–Heterocycles by the Transformation of Azidoacrylates", Monatshefte für Chemie 123, 1992, pp. 807–815.

Krutošiková et al., "Derivatives of Furo[3,2–b]pyrrole", Collect. Czech. Chem. Commun., vol. 59, 1994, pp. 473–481.

Krutošiková et al., "Reactions of Methyl 2–Formylfuro[3, 2–b]pyrrole–5–carboxylates", Chem. Papers. vol. 50, 1996, pp. 72–76.

Krutošiková et al., "Substituted Benzylfuro[3,2]pyrroles", Collect. Czech. Chem. Commun., vol. 57, 1992, pp. 1487–1494.

Krutošiková et al., "Substituted Vinyl Azides in Synthesis of Furo[3,2–b:4,5–b]–dipyrroles and Pyrrolo[2',3':4,5]Furo[3, 2–c]pyridines", Heterocycles. vol. 37, No. 3, 1994, pp. 1695–1700.

Krutošiková et al., "Substituted Vinyl Azides in the Synthesis of Condensed Nitrogen Heterocycles", Chem. Papers, vol. 48, 1994, pp. 268–273.

Krutošiková et al., "Synthesis and Reactions of Furo[3,2–b] pyurrole Type Aldehydes", Czech. Chem. Commun., vol. 58, 1993, pp. 2139–2149.

Murakami et al., "Direct Regioselective Vinylationof Indoles Using Palladium (II) Chloride", Heterocycles, 1984, vol. 22, No. 7, pp. 1493–1496.

Rosenmund et al., "Decarboxylierungen einiger 1–Alkyl–2–carboxy–3–indolessigsäuren sowie Synthese eines 5–Thiocyanato–2,3–dihydroindols", Chemical Berichte, 1975, vol. 108, pp. 3538–3542, XP–00909395.

Troschütz et al., "Synthesis of Substituted 4–Amino–4–cyano–1–oxo–1,2,510–tetrahydroazepino[3, 4–b]indoles", Journal of Heterocyclic Chemistry, Sep.–Oct. 1997, vol. 34, pp. 1431–1440, XP–000909451.

Yokoyama et al., "New Synthetic Method of Dehydrotryptophan Derivatives. Synthetic Studies on Indoles and Related Compounds, XXXIV[1]", Chemical and Pharmaceutical Bulletin, 1994, vol. 42, No. 4, pp. 832–838.

Yokoyama et al., "Palladium–catalyzed cross–coupling reaction: direct allylation of aryl bromides with allyl acetate" Tetrahedron Letters., vol. 26, No. 52–1985 pp. 6457–6460, XP002081581 Oxford GB * pp. 6458–6459: compound 7*.

* cited by examiner

INDOLE DERIVATIVES AND THEIR USE AS MCP-1 ANTAGONIST

This application is the National Phase of International Application PCT/GB00/00265 filed Jan. 31, 2000 which designated the U.S. and that International Application.

The present invention relates to anti-inflammatory compounds that act via antagonism of the CCR2 receptor, (also known as the MCP-1 receptor), leading inter alia to inhibition of Monocyte Chemoattractant Protein-1 (MCP-1). These compounds contain an indole moiety. The invention further relates to pharmaceutical compositions containing them, processes for their preparation, intermediates useful in their preparation and to their use as therapeutic agents.

MCP-1 is a member of the chemokine family of pro-inflammatory proteins which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glormerular nephritides, lung fibrosis, restenosis (International Patent Application WO 94/09128), alveolitis (Jones et al., 1992, *J. Immunol.*, 149, 2147) and asthma. Other disease areas where MCP-1 is thought to play a part in their pathology are atherosclerosis (e.g. Koch et al., 1992, *J. Clin. Invest.*, 90, 772–779), psoriasis (Deleuran et al., 1996, *J. Dermatological Science*, 13, 228–236), delayed-type hypersensitivity reactions of the skin, inflammatory bowel disease (Grimm et al., 1996, *J. Leukocyte Biol.*, 59,. 804–812), multiple sclerosis and brain trauma (Berman et al, 1996, *J. Immunol.*, 156,. 3017–3023). An MCP-1 inhibitor may also be useful to treat stroke, reperfusion injury, ischemia, myocardial infarction and transplant rejection.

MCP-1 acts through the CCR2 receptor. MCP-2 and MCP-3 may also act, at least in part, through this receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the CCR2 receptor.

The applicants have found a class of compounds containing an indole moiety which have useful inhibitory activity against MCP-1. Co-pending application UK 9716657.3 discloses a class of indoles with MCP-1 inhibitory activity. This application is based on the surprising discovery that particular substituted 5-hydroxy indoles are MCP-1 inhibitors which possess unexpected and beneficial properties with respect to potency and/or blood levels and/or bioavailability and/or solubility.

Accordingly, the present invention provides a compound of the formula (I):

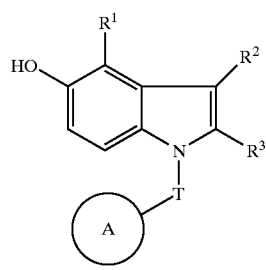

wherein:
$R^1$ is hydrogen, halo or methoxy;
$R^2$ is hydrogen, halo, methyl, ethyl or methoxy;
$R^3$ is carboxy, tetrazolyl or —CONHSO$_2R^4$ where $R^4$ is methyl, ethyl, phenyl, 2,5-dimethylisoxazolyl or trifluoromethyl;

T is —CH$_2$— or —SO$_2$—; and
ring A is 3-chlorophenyl, 4-chlorophenyl, 3-trifluoromethylphenyl, 3,4-dichlorophenyl, 3,4-difluorophenyl, 3-fluoro-4-chlorophenyl, 3-chloro-4-fluorophenyl or 2,3-dichloropyrid-5-yl; or a pharmaceutically acceptable salt or prodrug thereof.

In this specification the term "alkyl" includes both straight and branched chain alkyl groups but references to individual alkyl groups such as "propyl" are specific for the straight chain version only. The term "halo" refers to fluoro, chloro, bromo and iodo.

Particular novel compounds of the invention include, for example, compounds of the formula (I), or pharmaceutically-acceptable salts or prodrugs thereof, wherein, unless otherwise stated:

a) $R^1$ has any of the values defined in i)–iii) hereinafter or a combination of two of these values;

b) $R^2$ has any of the values defined in iv)–viii) hereinafter or a combination of two of these values;

c) $R^3$ has any of the values defined in ix)–xi) hereinafter or a combination of two of these values;

e) T has any of the values defined in xii)–xiii) hereinafter;

f) ring A has any of the values defined in xiv)–xxi) hereinafter or a combination of two or more of these values;

i) $R^1$ is hydrogen;
ii) $R^1$ is halo;
iii) $R^1$ is methoxy;
iv) $R^2$ is hydrogen;
v) $R^2$ is halo;
vi) $R^2$ is methyl;
vii) $R^2$ is ethyl;
viii) $R^2$ is methoxy;
ix) $R^3$ is carboxy;
x) $R^3$ is tetrazolyl;
xi) $R^3$ is —CONHSO$_2R^4$ where $R^4$ is methyl, ethyl, phenyl, 2,5-dimethylisoxazolyl or trifluoromethyl;
xii) T is —CH$_2$—;
xiii) T is —SO$_2$—;
xiv) Ring A is 3-chlorophenyl;
xv) Ring A is 4-chlorophenyl;
xvi) Ring A is 3-trifluoromethylphenyl;
xvii) Ring A is 3,4-dichlorophenyl;
xviii) Ring A is 3,4-difluorophenyl;
xix) Ring A is 3-fluoro-4-chlorophenyl;
xx) Ring A is 3-chloro-4-fluorophenyl; and
xxi) Ring A is 2,3-dichloropyrid-5-yl.

Preferably $R^1$ is hydrogen.
Preferably $R^2$ is hydrogen.
Preferably $R^3$ is carboxy.
Preferably T is —CH$_2$—.
Preferably Ring A is 3-chlorophenyl, 4-chlorophenyl, 3-trifluoromethylphenyl, 3,4-dichlorophenyl, 3,4-difluorophenyl, 3-fluoro-4-chlorophenyl or 3-chloro-4-fluorophenyl.

More preferably Ring A is 3,4-dichlorophenyl, 3-fluoro-4-chlorophenyl or 3-chloro-4-fluorophenyl.

For example, Ring A is 3,4-dichlorophenyl or 3-chloro-4-fluorophenyl.

In another aspect of the invention preferably Ring A is 3,4-dichlorophenyl, 2,3-dichloropyrid-5-yl or 3-chloro-4-fluorophenyl.

Therefore, in a preferred aspect of the invention there is provided a compound of formula (I) as depicted above wherein:
$R^1$ is hydrogen;
$R^2$ is hydrogen;

$R^3$ is carboxy;

T is —$CH_2$—; and

Ring A is 3,4-dichlorophenyl, 3-fluoro-4-chlorophenyl or 3-chloro-4-fluorophenyl, in particular 3,4-dichlorophenyl or 3-chloro-4-fluorophenyl; or a pharmaceutically acceptable salt or prodrug thereof.

Preferred compounds of the invention include any one of the Examples. More preferred compounds of the invention are Examples 1, 3 and 4, for instance, Example 1 and 3.

The invention further relates to all tautomeric forms of the compounds of formula (I).

It is also to be understood that certain compounds of the formula (I) can exist in solvated as well as unsolvated forms such as, for example, hydrated forms. It is to be understood that the invention encompasses all such solvated forms.

Compounds of formula (I) are inhibitors of monocyte chemoattractant protein-1. In addition, they appear to inhibit RANTES induced chemotaxis. RANTES (Regulated upon Activation, Normal T-cell Expressed and Secreted) is another chemokine from the same family as MCP-1, with a similar biological profile, but acting though the CCR1 receptor. As a result, these compounds can be used to treat disease mediated by these agents, in particular inflammatory disease.

Suitable pharmaceutically acceptable salts of compounds of formula (I) include base salts such as an alkali metal salt for example sodium, an alkaline earth metal salt for example calcium or magnesium; an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulphonate, fumarate, hydrochloride, hydrobromide, citrate, maleate and salts formed with phosphoric and sulphuric acid. There may be more than one cation or anion depending on the number of charged functions and the valency of the cations or anions. A preferred pharmaceutically acceptable salt is a sodium salt.

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include $C_{1-6}$alkyl esters, for example methyl or ethyl; $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; $C_{1-6}$alkoxycarbonyloxyethyl esters, for example 1-methoxycarbonyloxyethyl; aminocarbonylmethyl esters and mono- or di-N-($C_{1-6}$alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include $C_{1-6}$alkanoyl esters, for example acetyl esters; and benzoyl esters wherein the phenyl group may be substituted with aminomethyl or N- substituted mono- or di-$C_{1-6}$alkyl aminomethyl, for example 4-aminomethylbenzoyl esters and 4-N,N-dimethylaminomethylbenzoyl esters.

Further examples of such prodrugs are in vivo cleavable amides of a compound of the invention. Examples of such in vivo cleavable amides include an N—$C_{1-6}$alkylamide and an N,N-di-($C_{1-6}$alkyl)amide such as N-methyl, N-ethyl, N-propyl, N,N-dimethyl, N-ethyl-N-methyl or N,N-diethylamide Another aspect of the present invention provides a process for preparing a compound of formula (I) or a pharmaceutically acceptable salt or prodrug thereof which process (wherein $R^1$, $R^2$, $R^3$, T and Ring A are as defined for formula (I) unless otherwise stated) comprises of:

a) reacting compounds of formula (II):

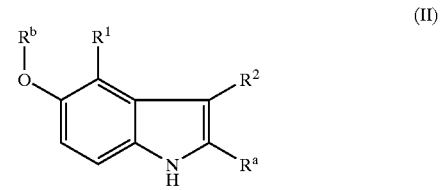

(II)

where $R^a$ is $R^3$ or protected $R^3$, and $R^b$ is hydrogen or a suitable hydroxy protecting group, with a compound of formula (III):

(III)

where L is a displaceable group;

and thereafter if necessary:

i) converting a compound of the formula (I) into another compound of the formula (I);

ii) removing any protecting groups; or iii) forming a pharmaceutically acceptable salt or prodrug thereof.

Suitable values for L are for example, a halogeno or sulphonyloxy group, for example a chloro, bromo, methanesulphonyloxy or toluene-4-sulphonyloxy group.

Specific reaction conditions for the above reactions are as follows.

a) Compounds of formula (II) and (III) may be reacted together in an inert solvent and a base such as N,N-dimethylformamide/sodium hydride or dichloromethane/sodium hydroxide or acetonitrile/potassium carbonate, or in the presence of a phase transfer catalyst such as tetra-n-butylammonium hydrogensulphate. The reaction is suitably carried out for 1–6 hours preferably 1–3 hours, at a temperature of 15–30° C., preferably 20–25° C. to give a compound of formula (I).

Compounds of formula (II) may be commercially available, or they may be made by modification using known processes of commercially available compounds of formula (II), or they may be prepared by the following processes:

Process i)
Reacting a Compound of Formula (IV)

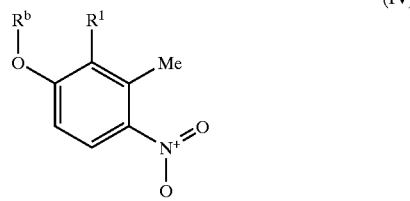

where $R^b$ is as defined above with a compound of formula (V)

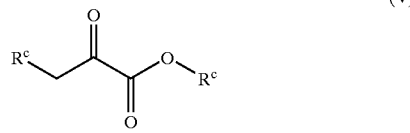

where $R^c$ is $C_{1-4}$alkyl.

Compounds of formula (IV) and (V) are reacted together under Reissert reaction conditions such as in an inert solvent (such as tetrahydrofuran), in the presence of a base (such as potassium ethoxide), at a temperature range of 15–30° C. preferably 20–25° C., for 10–20 hours preferably 15–17 hours. The resulting compound is isolated and dissolved in an alcohol stich as ethanol and an organic acid (such as acetic acid) and a transition metal catalyst (such as 10% Pd/C) and cyclohexene is added. The mixture is heated at a temperature of 60–120° C. preferably at 70–90° C. for 15–25 hours preferably 16–20 hours to give a compound of formula (II) wherein $R^a$ is —$CO_2C_{1-4}$alkyl.

Process (ii)
Reacting a Compound of Formula (VI)

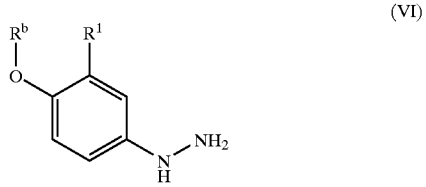

where $R^b$ is as defined above, with a compound of formula (VII):

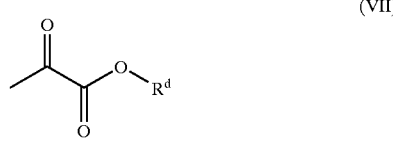

where $R^d$ is $C_{1-4}$alkyl.

Compounds of formula (VI) and (VII) are reacted together under Fischer conditions such as with an organic acid (such as acetic acid), in an alcohol (such as ethanol), at a temperature of 60–90° C., preferably 75–85° C., for 1–5 hours, preferably 1–3 hours. The resulting compound is mixed with a strong acid (such as polyphosphoric acid) and heated at 90–150° C. preferably 100–120° C., for 0.5–4 hours, preferably 0.5–2 hours to give a compound of formula (II) in which $R^2$ is hydrogen. Then, if desired, $R^2$ can be optionally converted into another value of $R^2$ as defined in formula (I) using techniques known in the art such as those described below.

Process (iii)
Cyclisation of a Compound of Formula (VIII)

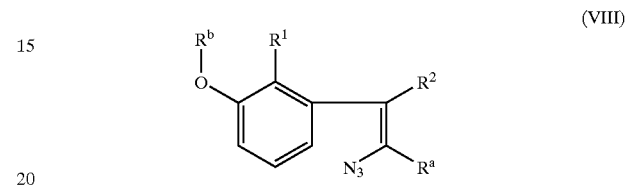

where $R^1$, $R^a$, $R^b$ and $R^2$ are as defined above.

Cyclisation may be effected by refluxing the compound in an organic solvent such as xylene. Compounds of formula (VIII) are suitably prepared by reacting a compound of formula (IX)

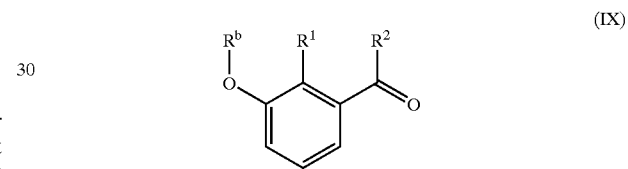

where $R^1$, $R^2$ and $R^b$ are as defined above, with a compound of formula (X)

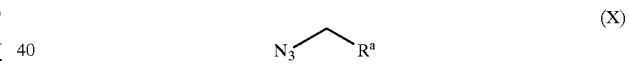

where $R^a$ is as defined above. The reaction is suitably effected in an organic solvent such as an alcohol, in particular methanol, in the presence of a base such as an alkali metal alkoxide, in particular sodium methoxide. Moderate temperatures of from −30 to 20° C. are suitably employed.

Process (iv)
In yet a further modification, compounds of formula (II) are prepared by cyclisation of a compound of formula (XI)

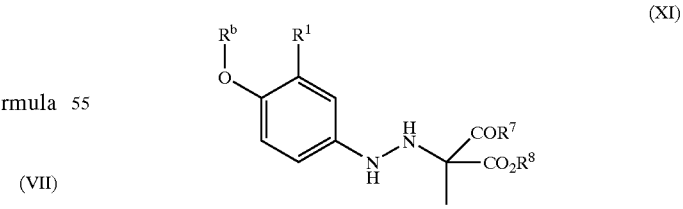

where $R^1$ and $R^b$ are as defined above, $R^7$ is alkyl, such as methyl, and $R^8$ is a carboxy protecting group such as alkyl, in particular methyl.

Cyclisation is suitably effected under Japp Klingemann conditions, by warming a solution of the compound in an organic solvent such as toluene and a suitable acid, such as p-toluene sulphonic acid.

Compounds of formula (XI) are suitably prepared by reacting a compound of formula (XII)

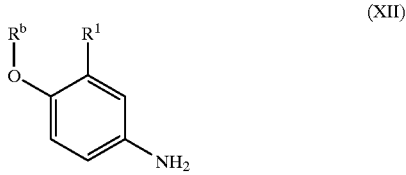

(XII)

where $R^1$, $R^b$, $R^5$ and $R^6$ are as defined above, with a compound of formula (XIII)

(XIII)

where $R^7$ and $R^8$ are as defined in relation to formula (XI). The compound of formula (XII) is suitably dissolved in a dilute acid such as 1.5N HCl in the presence of a nitrite such as sodium nitrite at moderately low temperatures from −30 to 0° C., preferably −5° C.

This solution is then mixed with a solution of a compound of formula (XIII) in an organic solvent such as ethanol, in the presence of a solution of a base such as an alkali metal hydroxide, for example aqueous sodium hydroxide solution.

Compounds of formula (III), (IV), (V), (VI), (VII), (VII), (X), (XII) and (XIII) are known or commercially available or are prepared by processes known in the art by standard manipulation of commercially available or known materials.

$R^c$ and $R^d$ are $C_{1-4}$alkyl. Preferably $R^c$ and $R^d$ are methyl or ethyl.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as carboxy or hydroxy it may be desirable to protect the group in some of the reactions mentioned herein.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Some of the intermediates described herein may be novel, for example intermediates of the formula (II), and as such they are provided as a further feature of the invention.

When a pharmaceutically-acceptable salt of a compound of formula (I) is required, it may be obtained, for example, by reaction of said compound with the appropriate acid (which affords a physiologically acceptable anion), or with the appropriate base (which affords a physiologically acceptable cation), or by any other conventional salt formation procedure.

According to a further aspect of the invention there is provided a pharmaceutical composition which comprises a compound of the formula (I) as defined hereinbefore or a pharmaceutically acceptable salt or prodrug thereof, in association with a pharmaceutically acceptable excipient or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents-and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents maybe, for example, naturally-occurring gums such as gum acaciaor gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example. from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

According to a further aspect of the present invention there is provided a compound of the formula (I) or a pharmaceutically acceptable salt or prodrug thereof, as defined hereinbefore for use in a method of treatment of the human or animal body by therapy. Conveniently, the invention provides a method of treating inflammatory disease by administering a compound of formula (I) or a pharmaceutically acceptable salt or prodrug or a pharmaceutical composition thereof, as described above.

A further feature of the present invention is a compound of formula (I) and pharmaceutically acceptable salt or prodrug thereof, for use as a medicament.

Conveniently this is a compound of formula (I), or a pharmaceutically acceptable salt or prodrug thereof, for use as a medicament for antagonising an MCP-1 mediated effect in a warm-blooded animal such as a human being.

Thus according to a further aspect of the invention there is provided the use of a compound of the formula (I), or a pharmaceutically acceptable salt or prodrug thereof, in the manufacture of a medicament for use in antagonising an MCP-1 mediated effect in a warm-blooded animal such as a human being.

According to a further feature of the invention there is provided a method of antagonising an MCP-1 mediated effect in a warm-blooded animal, such as a human being, in need of such treatment which comprises administering to said animal an effective amount of a compound of formula (I) or a pharmaceutically acceptable salt or prodrug thereof, as defined hereinbefore.

Biological Testing

The following biological test methods, data and Examples serve to illustrate the present invention.

| Abbreviations: | |
| --- | --- |
| ATCC | American Type Culture Collection, Rockville, USA. |
| BCA | Bicinchroninic acid, (used, with copper sulphate, to assay protein) |
| BSA | Bovine Serum Albumin |
| DMEM | Dulbecco's modified Eagle's medium |
| EGTA | Ethylenebis(oxyethylenenitrilo)tetraacetic acid |
| FCS | Foetal calf serum |
| HEPES | (N-[2-Hydroxyethyl]piperazine-N'-[2-ethane-sulphonic acid]) |
| HBSS | Hank's Balanced Salt Solution |
| hMCP-1 | Human Monocyte Chemoattractant Protein-1 |
| PBS | Phosphate buffered saline |
| PCR | Polymerase chain reaction |

AMPLITAQ™, available from Perkin-Elmer Cetus, is used as the source of thermostable DNA polymerase.

Binding Buffer is 50 mM HEPES, 1 mM $CaCl_2$, 5 mM $MgCl_2$, 0.5% foetal calf serum, adjusted to pH 7.2 with 1 M NaOH.

Non-Essential Amino Acids (100×concentrate) is: L-Alanine, 890 mg/l; L-Asparagine, 1320 mg/l; L-Aspartic acid, 1330 mg/l; L-Glutamic acid, 1470 mg/l; Glycine, 750 mg/l, L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt); 5000 units/ml; Streptomycin sulphate, 5000 μg/ml.

Human monocytic cell line THP-1 cells are available from ATCC, accession number ATCC TIB-202.

Hank's Balanced Salt Solution (HBSS) was obtained from Gibco; see *Proc. Soc. Exp. Biol. Med.,* 1949, 71, 196.

Synthetic cell culture medium, RPMI 1640 was obtained from Gibco; it contains inorganic salts [$Ca(NO_3)_2.4H_2O$ 100 mg/l; KCl 400 mg/l; $MgSO_4.7H_2O$ 100 mg/l; NaCl 6000 mg/l; $NaHCO_3$ 2000 mg/l & $Na_2HPO_4$ (anhyd) 800 mg/l], D-Glucose 2000 mg/l, reduced glutathione 1 mg/l, amino acids and vitamins.

FURA-2/AM is 1-[2-(5-carboxyoxazol-2-yl)-6-aminobenzofuran-5-oxy]-2-(2'-amino-5'-methylphenoxy)-ethane-N,N,N',N'-tetraacetic acid pentaacetoxymethyl ester and was obtained from Molecular Probes, Eugene, Oreg., USA.

Blood Sedimentation Buffer contains 8.5 g/l NaCl and 10 g/l hydroxyethyl cellulose.

Lysis Buffer is 0.15M $NH_4Cl^-$, 10 mM $KHCO_3$, 1 mM EDTA

Whole Cell Binding Buffer is 50 mM HEPES, 1 mM $CaCl_2$, 5 mM $MgCl_2$, 0.5% BSA, 0.01% $NaN_3$, adjusted to pH 7.2 with 1M NaOH.

Wash buffer is 50 mM HEPES, 1 mM $CaCl_2$, 5 mM $MgCl_2$, 0.5% heat inactivated FCS, 0.5MNaCl adjusted to pH7.2 with 1M NaOH.

General molecular biology procedures can be followed from any of the methods described in "Molecular Cloning—A Laboratory Manual" Second Edition, Sambrook, Fritsch and Maniatis (Cold Spring Harbor Laboratory, 1989).

i) Cloning and Expression of hMCP-1 Receptor

The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA,* 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (InVitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell,* 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.,* 6, 134). CHO-K1 clone 7 (CHO-CCR2B) was identified as the highest MCP-1 receptor B expresser.

ii) Preparation of Membrane Fragments

CHO-CCR2B cells were grown in DMEM supplemented with 10% foetal calf serum, 2 mM glutamine, 1×Non-Essential Amino Acids, 1×Hypoxanthine and Thymidine Supplement and Penicillin-Streptomycin (at 50 μg streptomycin/ml, Gibco BRL). Membrane fragments were prepared using cell lysis/differential centrifugation methods as described previously (Siciliano et al., 1990, *J. Biol. Chem.,* 265, 19658). Protein concentration was estimated by BCA protein assay (Pierce, Rockford, Ill.) according to the manufacturer's instructions.

iii) Assay $^{125}I$ MCP-1 was prepared using Bolton and Hunter conjugation (Bolton et al., 1973, *Biochem. J.,* 133, 529; Amersham International plc]. Equilibrium binding assays were carried out using the method of Ernst et al., 1994, *J. Immunol.,* 152, 3541. Briefly, varying amounts of $^{125}I$-labeled MCP-1 were added to 7 μg of purified CHO-CCR2B cell membranes in 100 μl of Binding Buffer. After 1 hour incubation at room temperature the binding reaction mixtures were filtered and washed 5 times through a plate washer (Brandel MLR-96T Cell Harvester) using ice cold Binding Buffer. Filter mats (Brandel GF/B) were pre-soaked for 60 minutes in 0.3% polyethylenimine prior to use. Following filtration individual filters were separated into 3.5 ml tubes (Sarstedt No. 55.484) and bound $^{125}I$-labeled MCP-1 was determined (LKB 1277 Gammamaster). Cold competition studies were performed as above using 100 pM $^{125}I$-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B receptor was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 μl) were tested in competition with 100 pM labelled MCP-1 over a concentration range (0.01–50 μM) in duplicate using eight point dose-response curves and $IC_{50}$ concentrations were calculated.

Compounds tested of the present invention had $IC_{50}$ values of 50 μM or less in the hMCP-1 receptor binding assay described herein.

b) MCP-1 Mediated Calcium Flux in THP-1 Cells

The human monocytic cell line THP-1 was grown in a synthetic cell culture medium RPMI 1640 supplemented with 10% foetal calf serum, 6 mM glutamine and Penicillin-Streptomycin (at 50 μg streptomycin/ml, Gibco BRL). THP-1 cells were washed in HBSS (lacking $Ca^{2+}$ and $Mg^{2+}$)+1 mg/ml BSA and resuspended in the same buffer at a density of $3 \times 10^6$ cells/ml. The cells were then loaded with 1 mM FURA-2/AM for 30 min at 37° C., washed twice in HBSS, and resuspended at $1 \times 10^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA, 1 mM $MgCl_2$ and 2 mM $CaCl_2$. The cuvette was placed in a fluorescence spectrophotometer (Perkin Elmer, Norwalk, Conn.) and pre-incubated for 4 min at 37° C. with stirring. Fluorescence was recorded over 70 sec and cells were stimulated by addition of hMCP-1 to the cuvette after 10 sec. $[Ca^{2+}]i$ was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic $[Ca^{2+}]$ according to the equation:

$$[Ca^{2+}]i = K_d \frac{(R - Rmin)}{(Rmax - R)}(Sf2/Sb2)$$

where the $K_d$ for FURA-2 $Ca^{2+}$ complex at 37° C. was taken to be 224 nm. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in $[Ca^{2+}]_i$ in a specific and dose dependent manner. Dose response curves indicated an approximate $EC_{50}$ of 2 nm. Test compounds dissolved in DMSO (10 μl) were assayed for inhibition of calcium release by adding them to the cell suspension 10 sec prior to ligand addition and measuring the reduction in the transient rise in $[Ca^{2+}]i$. Test compounds were also checked for lack of agonist activity by addition in place of hMCP-1.

c) hMCP-1 and RANTES Mediated Chemotaxis

In vitro chemotaxis assays were performed using the human monocytic cell line THP-1. Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, *Cancer Res.*, 48, 4827–4833).

Chemoattractants were introduced into a 96-well microtitre plate which forms the lower well of a chemotaxis chamber fitted with a PVP-free 5 μm poresize polycarbonate adhesive framed filter membrane (NeuroProbe MB series, Cabin John, Md. 20818, USA) according to the manufacturer's instructions. The chemoattractant was diluted as appropriate in synthetic cell culture medium, RPMI 1640 (Gibco) or supplemented with 2 mM glutamine and 0.5% BSA, or alternatively with HBSS with $Ca^{2+}$ and $Mg^{2+}$ without Phenol Red (Gibco) plus 0.1% BSA. Each dilution was degassed under vacuum for 30 min and was placed (400 μl) in the lower wells of the chamber and THP-1 cells ($5 \times 10^5$ in 100 μl RPMI 1640+0.5%BSA) were incubated in each well of the upper chamber. For the inhibition of chemotaxis the chemoanractant was kept at a constant submaximal concentration determined previously (1 nM MCP-1) and added to the lower well together with the test compounds dissolved in DMSO (final DMSO concentration<0.05% v/v) at varying concentrations. The chamber was incubated for 2 h at 37° C. under 5% $CO_2$. The medium was removed from the upper wells which were then washed out with 200 μl physiological saline before opening the chamber, wiping dry the membrane surface and centrifuging the 96-well plate at 600 g for 5 min to harvest the cells. Supernatant (150 μl) was aspirated and 10 μl of cell proliferation reagent, WST-1, {4-[3-(4-iodophenyl)-2-(4-nitrophenyl)-2H-5-tetrazolio]-1, 3-phenyl disulfonate} plus an electron coupling reagent (Boehringer Mannheim, Cat.no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

In an alternative form of the above assay, fluorescently tagged cells can be used in order to assist in end point detection. In this case, the THP-1 cells used are fluorescently tagged by incubation in the presence of 5 mM Calcein AM (Glycine, N,N'-[[3',6'-bis(acetyloxy)-3-oxospiro [isobenzofuran-1(3H),9'-[9H]xanthene]-2',7'-diyl]bis (methylene)]bis[N-[2-[(acetyloxy)methoxy]-2-oxoethyl]]-bis[(acetyloxy)methyl]ester; Molecular Probes) for 45 minutes in the dark. Cells are harvested by centrifugation and resuspended in HBSS (without Phenol Red) with $Ca^{2+}$, $Mg^{2+}$ and 0.1% BSA. 50 μl ($2 \times 10^5$ cells) of the cell suspension are placed on the filter above each well and, as above, the unit is incubated at 37° C. for 2 hours under 5% $CO_2$. At the end of the incubation, cells are washed off the upper face or the filter with phosphate buffered saline, the filter removed from the plate and the number of cells attracted to either the underside of the filter or the lower well estimated by readings fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and $IC_{50}$ of compounds under test and significance tests can be calculated. In addition to MCP-1 induced chemotaxis, this alternative form of the assay was also used to measure inhibition of RANTES (2 nM) induced chemotaxis.

d) Binding to Human Peripheral Blood Mononuclear Cells (PBMCs)

i) Preparation of Human PBMCs

Fresh human blood (200 ml) was obtained from volunteer donors, collected into sodium citrate anticoagulant to give a final concentration of 0.38%. The blood was mixed with Sedimentation Buffer and incubated at 37° C. for 20 minutes. The supernatant was collected and centrifuged at 1700 rpm for 5 minutes (Sorvall RT6000D). The pellet obtained was resuspended in 20 ml RPMI/BSA (1 mg/ml) and 4×5 mls of cells were carefully layered over 4×5 mls of Lymphoprepä (Nycomed) in 15 ml centrifuge tubes. Tubes were spun at 1700 rpm for 30 minutes (Sorvall RT6000D) and the resultant layer of cells was removed and transferred to 50 ml Falcon tubes. The cells were washed twice in Lysis Buffer to remove any remaining red blood cells followed by 2 washes in RPMI/BSA. Cells were resuspended in 5 mls of Binding Buffer. Cell number was measured on a Coulter counter and additional binding buffer was added to give a final concentration of $1.25 \times 10^7$ PBMCs/ml.

ii) Assay

[$^{125}$I]MCP-1 was prepared using Bolton and Hunter conjugation (Bolton et al., 1973, *Biochem. J.*, 133,529; Amersham International plc]. Equilibrium binding assays were carried out using the method of Ernst et al., 1994, *J. Immunol.*, 152, 3541. Briefly, 50 μl of $^{125}$I-labeled MCP-1 (final concentration 100 pM) was added to 40 μl ($5 \times 10^5$ cells) of cell suspension in a 96 well plate. Compounds, diluted in Whole Cell Binding Buffer from a stock solution of 10 mM in DMSO were added in a final volume of 5 μl to maintain a constant DMSO concentration in the assay of 5%. Total binding was determined in the absence of compound. Non-specific binding was defined by the addition of 5 μl cold MCP-1 to give a final assay concentration of 100 nM. Assay wells were made up to a final volume of 100 μl with Whole Cell Binding Buffer and the plates sealed. Following incubation at 37° C. for 60 minutes the binding reaction mixtures were filtered and washed for 10 seconds using ice cold Wash Buffer using a plate washer (Brandel MLR-96T Cell Harvester). Filter mats (Brandel GF/B) were pre-soaked for 60 minutes in 0.3% polyethylenimine plus 0.2% BSA prior to use. Following filtration individual filters were separated into 3.5 ml tubes (Sarstedt No. 55.484) and bound $^{125}$I-labeled MCP-1 was determined (LKB 1277 Gammamaster).

Test compound potency was determined by assay in duplicate using six point dose-response curves and $IC_{50}$ concentrations were determined.

No physiologically unacceptable toxicity was observed at the effective dose for compounds tested of the present invention.

The invention is further illustrated, but not limited by the following Examples in which the following general procedures were used unless stated otherwise.

i) N,N-Dimethylformamide (DMF) was dried over 4 Å molecular sieves. Anhydrous tetrahydrofuran (THF) was obtained from Aldrich SURESEAL™ bottles. Other commercially available reagents and solvents were used without further purification unless otherwise stated. Organic solvent extracts were dried over anhydrous $MgSO_4$.

ii) $^1H$, $^{13}C$ and $^{19}F$ NMR were recorded on Bruker WM200, WM250, WM300 or WM400 instruments using DMSO-$d_6$ with $Me_4Si$ or $CCl_3F$ as internal standard as appropriate, unless otherwise stated. Chemical shifts are quoted in d (ppm) and peak multiplicities are designated as follows: s, singlet; d, doublet; dd, doublet of doublets; t, triplet; dt, doublet of triplets; q, quartet; m, multiplet; br, broad.

iii) Mass spectra were recorded on VG 12-12 quadrupole, VG 70-250 SE, VG ZAB 2-SE or a VG modified AEI/Kratos MS9 spectrometers.

iv) For TLC analysis, Merck precoated TLC plates (silica gel 60 F254, d=0.25 mm) were used.

v) Flash chromatography was performed on silica (Merck Kieselgel: Art.9385).

EXAMPLE 1

N-(3,4-Dichlorobenzyl)-5-hydroxyindole-2-carboxylic acid

Sodium hydroxide (2M, 3 ml) was added to a stirred solution of ethyl N-(3,4-dichlorobenzyl)-5-hydroxyindole-2-carboxylate (0.1 g) in THF (3 ml) and methanol (1.5 ml). The reaction was stirred at ambient temperature for 4 hours. The reaction was concentrated in vacuo and the residue was dissolved in water (5 ml). The solution was acidified by the addition of aqueous hydrochloric acid (2M, 4 ml) precipitating the product as a white solid. The product was filtered, washed with water and dried in vacuo to yield the title compound (82 mg, 89%). NMR: δ 5.77 (s, 2H), 6.81 (dd, 1H), 6.89 (dd, 1H), 6.95 (d, 1H), 7.13 (s, 1H), 7.26 (d, 1H), 7.34 (d, 1H), 7.52 (d, 1H), 9.01 (s, 1H), 12.85 (s, 1H); m/z 334 (M–H$^+$).

The procedure described in the above example were repeated using the appropriate starting ethyl indole-2-carboxylates. Thus were obtained the compounds described below.

EXAMPLE 2

N-[(2,3-Dichloropyrid-5-yl)methyl]-5-hydroxyindole-2-carboxylic acid

36% yield. NMR(CD$_3$SOCD$_3$) δ 5.80 (s, 2H), 6.84 (dd, 1H), 6.96 (d, 1H), 7.14 (s, 1H), 7.23 (d, 1H), 7.73 (d, 1H), 8.06 (d, 1H); m/z 339 (M–H$^+$) 337, 335.

EXAMPLE 3

N-(3-Chloro-4-fluorobenzyl)-5-hydroxyindole-2-carboxylic acid

68% yield. NMR(CD$_3$SOCD$_3$) δ 5.75 (s, 2H), 6.82 (dd, 1H), 6.95 (m, 2H), 7.12 (s, 1H), 7.2–7.4 (m, 3H); m/z 320 (M–H$^+$), 318.

EXAMPLE 4

N-(4-Chloro-3-fluorobenzyl)-5-hydroxyindole-2-carboxylic acid

94% yield. NMR(CD$_3$SOCD$_3$) δ 5.78 (s, 2H), 6.78 (dd, 1H), 6.80 (dd, 1H), 6.96 (d, 1H), 7.03 (dd, 1H), 7.12 (s, 1H), 7.31 (d, 1H), 7.43 (t, 1H); m/z 318 (M–H$^+$).

EXAMPLE 5

N-(3-Chlorobenzyl)-5-hydroxyindole-2-carboxylic acid

75% yield. m/z 300 (M–H$^+$).

EXAMPLE 6

N-(3-Trifluromethylbenzyl)-5-hydroxyindole-2-carboxylic acid

81% yield. m/z 334 (M–H$^+$).

EXAMPLE 7

N-(4-Chlorobenzyl)-5-hydroxyindole-2-carboxylic acid

82% yield. m/z 300 (M–H$^+$).

EXAMPLE 8

3-Bromo-N-(3,4-Dichlorobenzyl)-5-hydroxyindole-2-carboxylic acid

95% yield. m/z 414 (M–H$^+$).

EXAMPLE 9

4-Bromo-N-(3,4-dichlorobenzyl)-5-hydroxyindole-2-carboxylic acid

96% yield. NMR(CD$_3$SOCD$_3$) δ 5.78 (s, 2H), 6.86 (dd, 1H), 7.01 (d, 1H), 7.04 (s, 1H), 7.33 (s, 1H), 7.40 (d, 1H), 7.52 (d, 1H), 9.78 (s, 1H), 13.10 (bs, 1H); m/z 414 (M–H$^+$).

EXAMPLE 10

N-(3,4-Dichlorobenzyl)-5-hydroxy-3-methylindole-2-carboxylic acid

73% yield. NMR(CD$_3$SOCD$_3$) δ 2.44 (s, 3H), 5.69 (s, 2H), 6.83 (m, 2H), 6.92 (d, 1H), 7.25 (d, 1H), 7.30 (d, 1H), 7.50 (d, 1H), 9.00 (s, 1H), 12.90 (bs, 1H); m/z 350 (M–H$^+$).

EXAMPLE 11

N-(3,4-dichlorobenzyl)-4-fluoro-5-hydroxyindole-2-carboxylic acid

68% yield. NMR(CD$_3$SOCD$_3$) δ 5.80(s, 2H), 6.88(m, 1H), 7.00(t, 1H), 7.20(m, 2H), 7.32(m,1H), 7.50(m, 1H), 9.25(s, 1H), 13.10(s, 1H); M/z(M–H$^+$) 351.9

EXAMPLE 12

N-(3,4-dichlorobenzyl)3-methoxy-5-hydroxyindole-2-carboxylic acid

73% yield. NMR(CD$_3$SOCD$_3$) δ 4.3 (s, 3H), 5.7 (s, 2H), 6.9 (m, 2H), 7.1–7.4 (m, 4H); m/z 364,366(M–H+)

EXAMPLE 13

N-(3,4-dichlorobenzyl)-3-chloro-5-hydroxyindole-2-carboxylic acid

97% yield. NMR(CD$_3$SOCD$_3$) δ 5.75 (s, 2H), 6.9 (m, 3H), 7.3 (s, 1H), 7.45 (d, 1H), 7.5 (d, 1H), 9.35 (s, 1H); m/z 368 (M–H$^+$).

EXAMPLE 14

N-(3,4-dichlorobenzyl)-4-chloro-5-hydroxyindole-2-carboxylic acid

83% yield. NMR(CD$_3$SOCD$_3$) δ 5.79 (s, 2H), 6.88 (dd, 1H), 7.01 (d, 1H), 7.11 (s, 1H), 7.3 (d, 1H), 7.38 (d, 1H), 7.51 (d, 1H), 9.67 (bs, 1H); m/z 368.2 (M–H$^+$)

Preparation of Starting Materials

The starting materials for the Examples above are either commercially available or are readily prepared by standard methods from known materials. For example the following reactions (Methods A–J) are illustrations but not limitations of the preparation of the starting materials used in the above reactions.

Method A

3-Chloro-4-fluorobenzyl bromide

A solution of 3-chloro-4-fluorobenzaldehyde (3 g) in THF (40 ml) was added over 2 minutes to a stirred suspension of sodium borohydride (1.07 g) in methanol (40 ml) at 0° C. The mixture was allowed to warm to room temperature and then quenched with water. The resulting suspension was partitioned between water and diethyl ether and the combined organic extracts were dried and concentrated in vacuo. The residue was dissolved in dichloromethane (90 ml) and triphenylphosphine (4.62 g) and tetrabromomethane (6.64 g) were added at 0° C. The mixture was allowed to warm to room temperature overnight then concentrated in vacuo and the residue purified by column chromatography using isohexane as eluent to yield the desired product (3.57 g, 85%). NMR: δ 4.7 (s, 2H), 7.4 (m, 2H), 7.7 (m, 1H).

In a similar manner but starting from 3-fluoro-4-chlorobenzaldehyde was prepared:

3-Fluoro-4-chlorobenzyl bromide

74% yield. NMR: δ 4.5(s, 2H), 7.1(t, 1H), 7.25(m,1H), 7.45(dd, 1H).

Method B

2,3-Dichloro-5-(hydroxymethyl)pyridine

Borane-tetrahydrofuran complex (1M solution in tetrahydrofuran, 52 ml) was added to a stirred solution of 5,6-dichloronicotinic acid (2 g) in tetrahydrofuran (60 ml) over 20 minutes at 0° C. The reaction mixture was allowed to warm to room temperature over 90 minutes and then cooled to 0° C. and quenched with water (100 ml). The solution was saturated with solid sodium chloride and extracted with ethyl acetate and the combined organic extracts were dried and concentrated in vacuo. The residue was triturated with dichloromethane-50% ethyl acetate and the solid by-product was removed by filtration. The filtrate was concentrated in vacuo and purified by column chromatography using isohexane/ethyl acetate (1:1 v/v) as eluent to yield the product as a white solid (820 mg, 45%). NMR: δ 4.55 (d, 2H), 5.5 (t, 1H), 8.0 (m, 1H), 8.3 (m, 1H); m/z 178.1 (M+H$^+$).

Method C

2,3-Dichloro-5-(bromomethyl)pyridine 2,3-Dichloro-5-(hydroxymethyl)pyridine (275 mg) was dissolved in dichloromethane (10 ml) and stirred in the presence of triphenylphosphine (444 mg) and tetrabromomethane (641 mg) overnight. The solution was concentrated in vacuo and the residue purified by column chromatography using isohexane: 2.5% ethyl acetate as eluent to yield the product as a white solid (270 mg, 73%). NMR: δ 4.75 (s, 2H), 8.25 (m, 1H), 8.5 (m, 1H); m/z 242 (M+H$^+$).

Method D

Ethyl 5-acetoxy-N-(3,4-dichlorobenzyl)indole-2-carboxylate i) Ethyl 5-hydroxyindole-2-carboxylate Boron tribromide (64.58 g) was added dropwise to a stirred solution of ethyl 5-methoxyindole-2-carboxylate (20 g) in dichloromethane (1000 ml) at –78° C. under an atmosphere of argon. The reaction was allowed to warm to room temperature and stirred for a further 2 hours. The reaction was poured into ice/saturated aqueous sodium hydrogen carbonate solution with stirring and extracted with ethyl acetate. Combined organic extracts were washed with saturated aqueous sodium hydrogen carbonate solution, water, aqueous saturated sodium chloride solution and dried. The solution was concentrated in vacuo and the residue was purified by column chromatography using 0–60% diethyl ether: iso-hexane as eluent to yield product as a white solid (9.02 g, 48%). NMR: δ 1.31) (t, 3H), 4.29 (q, 2H), 6.79 (dd, 1H), 6.90 (dd. 1H), 7.22 (d, 1H), 8.84 (s, 1H), 11.52 (brs, 1H); m/z 206 (M+H$^+$).

ii) Ethyl 5-acetoxyindole-2-carboxylate

A stirred solution of ethyl 5-hydroxyindole-2-carboxylate (7.79 g) and 4-dimethylaminopyridine (20 mg) in acetic anhydride (80 ml) was heated at 80° C. for 4 hours. The reaction was concentrated in vacuo and the residue was dissolved in ethyl acetate. Combined organic extracts were washed with hydrochloric acid (2 M), saturated aqueous sodium hydrogen carbonate solution, water, aqueous saturated sodium chloride solution and dried. The solution was concentrated in vacuo to yield the product as a yellow solid (9.39 g,100%). NMR: δ 1.20 (t, 3H), 2.10 (s, 3H), 4.19 (q, 2H), 6.86 (dd, 1H), 6.97 (d, 1H), 7.20 (s, 1H), 7.29 (d, 1H); m/z 248 (M+H$^+$).

iii) Ethyl 5-acetoxy-N-(3,4-dichlorobenzyl)indole-2-carboxylate 3,4-Dichlorobenzyl bromide (5.96 g) was added to a stirred solution of ethyl 5-acetoxyindole-2-carboxylate (5.4 g) and potassium carbonate (6.94 g) in acetonitrile (500 ml) under an atmosphere of argon. The reaction was heated at 80° C. for 16 hours, then concentrated in vacuo and the residue partitioned between ethyl acetate and water. Combined organic extracts were washed with water, saturated aqueous sodium chloride and dried. The solvent was removed in vacuo and the residue was triturated with iso-hexane to yield the product as a cream solid (5.55 g, 63%). NMR: δ 1.27 (t, 3H), 2.27 (s, 3H), 4.28 (q, 2H), 5.82 (s, 2H), 6.90 (d, 1H), 7.09 (dd, 1H), 7.33–7.40 (m, 2H), 7.46 (d, 1H) 7.52 (d, 1H), 7.60 (d, 1H).

The procedures described in Method D i)–iii) were repeated using the appropriate benzyl halide or, using the alkyl indole-2-carboxylates as prepared by method F&G, with the appropriate benzyl halide. Thus were obtained the compounds described below.

Method D1

Ethyl 5-acetoxy-N-[(2,3-dichloropyrid-5-yl)methyl]indole-2carboxylate

90% yield. NMR: δ 1.27 (t, 3H), 2.26 (s, 3H), 4.28 (q, 2H), 5.85 (s, 2H), 7.12 (dd, 1H), 7.38 (s, 1H), 7.47 (d, 1H), 7.68 (d, 1H), 7.78 (d, 1H), 8.10 (d, 1H); m/z 409 (M+H$^+$), 407.

Method D2

Ethyl 5-acetoxy-N-(3-chloro4-fluorobenzyl)indole-2-carboxylate

57% yield. NMR (CDCl$_3$): δ 1.37 (t, 3H), 2.33 (s, 3H), 4.35 (q, 2H), 5.74 (s, 2H), 6.90 (m, 1H), 7.00 (d, 1H), 7.05 (dd, 1H), 7.13 (dd, 1H), 7.26 (d, 1H), 7.36 (s, 1H), 7.22 (d, 1H).

Ethyl 5-acetoxy-N-(4-chloro-3-fluorobenzyl)indole-2-carboxylate

73% yield. m/z 390 (MH$^+$).

Ethyl 5-acetoxy-N-(3-chlorobenzyl)indole-2-carboxylate

93% yield. m/z 372 (MH$^+$).

Ethyl 5-acetoxy-N-(3-trifluoromethylbenzyl)indole-2-carboxylate

91% yield. m/z 406 (MH$^+$).

Ethyl 5-acetoxy-N-(4-chlorobenzyl)indole-2-carboxylate

70% yield. m/z 372 (MH$^+$).

Ethyl 5-acetoxy-3-bromo-N-(3,4-dichlorobenzyl)indole-2-carboxylate

86% yield. m/z 486 (MH$^+$).

Ethyl 5-acetoxy-4-bromo-N-(3,4-dichlorobenzyl)indole-2-carboxylate

62% yield. NMR δ 1.40 (t, 3H), 2.39 (s, 3H), 4.38 (q, 2H), 5.77 (s, 2H), 6.82 (dd, 1H), 7.08 (d, 1H), 7.18 (s, 1H), 7.22 (d, 1H), 7.32 (d, 1H), 7.42 (s, 1H); m/z 486 (MH$^+$).

Ethyl 5-acetoxy-N-(3,4-dichlorobenzyl)-3-methylindole-2-carboxylate

79% yield. NMR δ 1.40 (t, 3H), 2.36 (s, 3H), 2.40 (s, 3H), 4.35 (q, 2H), 5.76 (s, 2H), 6.83 (dd, 1H), 7.00 (d, 1H), 7.10 (d, 1H), 7.19 (s, 1H), 7.30 (d, 1H), 7.40 (s, 1H); m/z 421 (M+H$^+$).

Ethyl 5-acetoxy-N-(3,4-dichlorobenzyl)-3-chloroindole-2-carboxylate

83% yield. NMR δ 1.25 (t, 3H), 2.25 (s, 3H), 4.3 (q, 2H), 5.8 (s, 2H), 6.9 (d, 1H), 7.2 (m, 1H), 7.4 (m, 2H), 7.5 (d, 1H), 7.7 (d, 1H); m/z 441.8 (M+H$^+$).

Method E

Ethyl N-(3,4-dichlorobenzyl)-5-hydroxyindole-2-carboxylate

Sodium ethoxide (1.86 g) was added to a stirred solution of ethyl 5-acetoxy-N-(3,4-dichlorobenzyl)indole-2-carboxylate (5.55 g) in ethanol (50 ml) under an atmosphere of argon. The reaction was stirred at room temperature for 2 hours, then concentrated in vacuo and the residue acidified with aqueous hydrochloric acid (2 M) and extracted with dichloromethane. Combined organic extracts were washed with water, saturated aqueous sodium chloride solution and dried. The solvent was removed in vacuo and the residue was triturated with hexane/diethyl ether to yield the product as a white solid (3.17 g, 92%). NMR: δ 1.26 (t, 3H), 4.25 (q, 2H), 5.75 (s, 2H), 6.81–6.91 (m, 2H), 6.98 (d, 1H), 7.19 (s, 1H), 7.29 (d, 1H), 7.38 (d, 1H) 7.50 (d, 1H), 9.06 (s, 1H); m/z 364 (M+H$^+$).

Method F

Ethyl 5-acetoxy-3-bronmoindole-2-carboxylate

N-Bromosuccinimide (0.14 g) was added to a stirred solution of ethyl 5-acetoxyindole-2-carboxylate (0.2 g) in DMF (3.0 ml). The reaction was stirred for 4 hours, then poured into water. The resulting precipitate was filtered and dried in vacuo to give the title compound as a white powder (0.23 g, 87%). NMR δ 1.38 (t, 3H), 2.23 (s, 3H), 4.38 (q, 2H), 7.10 (dd, 1H), 7.23 (d, 1H), 7.50 (d, 1H), 12.28 (bs, 1H); m/z 326 (M$^+$).

Method F1

Ethyl 5-acetoxy-3-chloroindole-2-carboxylate

A solution of ethyl 5-acetoxyindole-2-carboxylate (500 mg) in dichloromethane (10 ml) was stirred at room temperature in the presence of N-chlorosuccinimide (297 mg) and potassium carbonate (279 mg) overnight. The resulting precipitate was collected by filtration, washed with cold dichloromethane followed by water and dried under vacuum overnight to give the desired product as a white powder (425 mg, 75%). NMR: δ 1.35 (t,3H), 2.25 (s,3H), 4.4 (q,2H), 7.1 (d,1H), 7.3 (s, 1H), 7.5 (d, 1H), 12.2 (s, 1H); m/z 281.9 (M+H$^+$).

Method G

Ethyl 5-acetoxy-3-methylindole-2-carboxylate
(i) Ethyl 5-methoxy-3-methylindole-2-carboxylate
Concentrated sulphuric acid (1 ml) was added to a solution of 4-methoxyphenyl hydrazine hydrochloride (11.2 g) and 2-oxobutyric acid (8.72 g) in ethanol (250 ml), and the solution heated at reflux for 16 hours. The reaction was cooled, concentrated in vacuo, and the residue triturated with ethanol to give the title compound as a white solid (8.8 g, 59%). NMR δ 1.36 (t, 3H), 3.76 (s, 3H), 4.30 (q, 2H), 6.88 (dd, 1H), 7.03 (d, 1H), 7.28 (d, 1H), 11.28 (bs, 1H); m/z 232 (M–H$^+$).

(ii) Ethyl 5-acetoxy-3-methylindole-2-carboxylate
Boron tribromide (25 g) was added dropwise to a stirred solution of ethyl 5-methoxy-3-methylindole-2-carboxylate (2.0 g) in dry dichloromethane (250 ml) at –78° C. under an atmosphere of argon. The reaction was allowed to warm to room temperature and stirred for a further 2 hours. The reaction was poured into ice/saturated aqueous sodium hydrogen carbonate solution with stirring and extracted with ethyl acetate. Combined organic extracts were washed with saturated aqueous to sodium hydrogen carbonate solution, water, aqueous saturated sodium chloride solution and dried (MgSO$_4$). The solution was concentrated in vacuo and the residue dissolved in ethyl acetate. DMAP (20 mg) and acetic anhydride (0.5 ml) were added and the solution heated at reflux for 5 minutes. The reaction was cooled, concentrated in vacuo and the residue triturated with ether to give the title compound as a white powder (0.4 g, 18%). NMR δ 1.37 (t, 3H), 2.25 (s, 3H), 2.50 (s, 3H), 4.34 (q, 2H), 7.00 (dd, 1H), 7.37 (d, 1H), 7.40 (d, 1H), 11.52 (bs, 1H); m/z 260 (M–H$^+$).

In a similar manner but starting with ethyl 4-bromo-5-methoxyindole-2-carboxylate was prepare:

Ethyl 5-acetoxy-4-bromoindole-2-carboxylate NMR δ 1.42(t, 3H), 2.39(s, 3H), 4.42(q, 2H), 7.02(d, 1H), 7.23(s, 1H), 7.35(d, 1H), 9.22(bs, 1H): m/z 374,326 (M–H$^+$).

Method H

Methyl-N-(3,4-dichlorobenzyl)-4-fluoro-5-hydroxyindole-2-carboxylate
(i) 2-Fluoro-3-benzyloxy benzaldehyde
2-Fluoro-3-hydroxybenzaldehyde (16.49 g) was dissolved in dimethylformamide (200 ml) and stirred under an argon atmosphere. Sodium hydride was added (60% in mineral oil, 5.18 g) and the mixture was stirred for 30 minutes. Benzyl bromide was added (16.8 ml) and the mixture was stirred overnight. Reaction mixture was concentrated in vacuo and the resulting residue was partitioned between diethyl ether (200 ml) and water (200 ml). Combined organic extracts were washed with water (400 ml), dried (MgSO$_4$) and concentrated in vacuo. The residue was purified by flash column chromatography, using a gradient of 0–10% ethyl acetate/iso-hexane as eluent to give the product as a yellow solid (18.41 g) $^1$H NMR (DMSO-d$_6$) δ 5.20(s, 2H), 7.2–7.6(m, 8H), 10.21(s, 1H)

(ii) Methyl-2-azido-3-(2-fluoro-3-benzyloxyphenyl) propenoate
A mixture of methylazidoacetate (36.64 g) and 2-Fluoro-3-benzyloxy benzaldehyde (18.32 g) in methanol (250 ml) was added dropwise, with stirring, over 1 hour to a mixture of sodium methoxide (17.20 g) in methanol (100 ml) at –25° C. under a stream of argon. Mixture was left to stir for 20 minutes, allowed to warm to 5° C. and stirred overnight.

Resulting precipitate was filtered, then washed sequentially with cold methanol, dilute solution of acetic acid in water and water. Resulting solid was dried under vacuum to give the product as a pale brown solid (16.70 g) which was used without purification.

(iii) Methyl-4-fluoro-5-benzyloxyindole-2-carboxylate
A solution of methyl-2-azido-3-(2-fluoro-3-benzyloxyphenyl)propenoate (16.7 g) in xylene (600 ml) was added dropwise with stirring to refluxino xylene (2.4 L) over 1 hour and then stirred for a further 20 minutes. The reaction mixture was concentrated in vacuo and purified by flash column chromatography, using a gradient of 0–100% ethyl acetate/iso-hexane as eluent to give the product as a yellow solid (12.93 g) $^1$H NMR (DMSO-d$_6$) δ 3.85(s, 3H), 5.15(s, 2H), 7.05–7.45(m, 8H), 12.06(s, 1H); M/z(+) 300.4 (MH$^+$)

(iv) Methyl-N-(3,4-dichlorobenzyl)-4-fluoro-5-benzyloxyindole-2-carboxylate
Sodium hydride (60% in mineral oil, 589 mg) was added to a solution of methyl-4-fluoro-5-benzyloxyindole-2-carboxylate (4 g) in dimethylformamide (100 ml) and the mixture was stirred under an argon atmosphere for 30 minutes. 3,4-dichlorobenzyl chloride (2.22 ml) was added and the mixture stirred overnight. The reaction mixture was concentrated in vacuo and the residue partitioned between diethyl ether (100 ml) and water (100 ml). Organic extracts were washed with water (100 ml), dried (MgSO4), concentrated in vacuo and purified by flash column chromatography; using iso-hexane followed by 5% ethyl acetate/iso-hexane as eluent, to give the product as a yellow crystalline solid (4.61 g) $^1$H NMR (DMSO-d$_6$) δ 3.80(s, 3H), 5.15(s, 2H), 5.80(s, 2H), 6.85(m, 1H), 7.25–7.52(m, 10H); M/z(+) 458.2 (MH$^+$)

(v) Methyl-N-(3,4-dichlorobenzyl)-4fluoro-5-hydroxyindole-2-carboxylate
A mixture of methyl-N-(3,4-dichlorobenzyl)-4-fluoro-5-benzyloxyindole-2-carboxylate (8.22 g) and 5% Pd/C (200 mg) in ethyl acetate (250 ml) was stirred under a hydrogen atmosphere overnight, filtered through celite, concentrated in vacuo and purified by flash column chromatography using a gradient of 0–50% ethyl acetate/iso-hexane as eluent to give the product as a brown solid (6.18 g) $^1$H NMR (DMSO-d$_6$) δ3.80(s, 3H), 5.75(s, 2H), 6.85(m, 1H), 7.00(t, 1H), 7.22(m, 2H), 7.30(m, 1H), 7.50(m,1H), 9.33(s, 1H); M/z(–) 366.2 (MH$^-$)

Method I

Ethyl-N-(3,4-dichlorobenzyl) 3-methoxy-5-hydroxyindole-2-carboxylate
(i) Ethyl 5-benzyloxy diazoindole-2-carboxylate
Sodium nitrite (6 g) was added portionwise to a solution of ethyl 5-benzyloxyindole-2-carboxylate in ethyl acetate (40 ml) and acetic acid (20 ml). The mixture was stirred for 18 hours and then partitioned between ethyl acetate and water. The organic extracts were washed with water, saturated aqueous sodium hydrogen carbonate and dried. The solvent was removed in vacuo and the resulting gum was titurated with diethyl ether to give the product as an orange powder (1.8 g)NMR: δ1.45 (t, 3H), 4.5 (q, 2H), 5.1 (s, 2H), 7.05 (m, 2H), 7.3 (m, 5H), 7.9 (d, 1H); m/z 322 (M+H$^+$)

(ii) Ethyl 3-methoxy-5-benzyloxy indole-2-carboxylate
Rhodium octanoate (300 mg) was added to a stirred solution of ethyl 5-benzyloxy diazoindole-2-carboxylate (2.0 g) in toluene (100 ml) and methanol (10 ml). The mixture was refluxed under an inert atmosphere for 2.5 hours. The solution was concentrated in vacuo and the residue purified by column chromatography using 30–50% diethyl ether/iso-hexane to give an orange solid (1.41 g).NMR: δ 1.4 (t, 3H), 4.05 (s, 3H), 4.4 (q, 2H), 5.1 (s, 2H), 7.1 (dd, 1H), 7.2–7.5 (m, 8H); m/z 326 (MH$^+$)

(iii) Ethyl-N-(3,4-dichlorobenzyl)3-methoxy-5-benzyloxy indole-2-carboxylate
3,4 Dichlorobenzyl chloride (0.72 ml) was added to a stirred solution of ethyl 3-methoxy-5-benzyloxyindole-2- carboxylate (1.40 g), potassium carbonate (0.90 g) and potassium iodide (0.1 g) in DMF (50 ml) under inert atmosphere. The reaction mixture was heated to 50° C. for 6 hours, then partitioned between ethyl acetate and water. Combined organic extracts were washed with water, then 3 times with saturated aqueous sodium chloride solution and dried. The solvent was removed in vacuo and the residue purified by column chromatography using 10–30% ethyl acetate/iso-hexane to give a yellow oil (0.9 g). NMR: δ 1.4 (t, 3H), 4.0 (s, 3H), 4.4 (q, 2H), 5.1 (s, 2H), 5.6 (s, 2H), 6.9 (dd, 1H), 7.0–7.5 (m, 9H); m/z 484 (MH$^+$)

(iv) Ethyl-N-(3,4-dichlorobenzyl)3-methoxy-5-hydroxyindole-2-carboxylate

5% Pd/C (100 mg) was added to a stirred solution of ethyl-N-(3,4-dichlorobenzyl)3-methoxy-5-benzyloxyindole-2-carboxylate (0.9 g) in ethyl acetate (50 ml) and the mixture was hydrogenated for 12 hours. Catalyst filtered off and filtrate evaporated to give a brown oil (0.61 g) which was used without further purification. NMR: δ 1.4 (t, 3H), 4.0 (s, 3H), 4.4 (q, 2H), 5.6 (s, 2H), 6.8 (dd, 1H), 6.9 (dd, 1H), 7.1 (m, 3H), 7.3 (d,1H); m/z 394 (MH$^+$)

Method J

Ethyl N-(3,4-dichlorobenzyl)-4-chloro-5-methoxyindole-2-carboxylate (i) Ethyl-2-azido-3-(2-chloro-3-methoxyphenyl)pronenoate A solution of ethyl azidoacetate (9.9 g) and 2-chloro-3-methoxybenzaldehyde (3 g) in ethanol (20 ml) was added dropwise to a solution of sodium ethoxide (4.7 g) in ethanol (10 ml) at 0° C. The reaction was allowed to warm to ambient temperature over 18 hours then partitioned between 2N HCl (50 ml) and dichloromethane (250 ml). The organic phase was dried (MgSO4), concentrated under vacuo and the residue purified by column chromatography using isohexane −12% ethylacetate/isohexane as eluent to give the product as a pale yellow crystalline solid (2.2 g, 44%), This was used without further purification (ii) Ethyl-4-chloro-5-methoxyindole-2-carboxylate A solution of ethyl-2-azido-3-(2-chloro-3-methoxyphenyl)propenoate (2.22 g) in xylene (100 ml) was heated at reflux for 30 minutes, concentrated in vacuo and the residue purified by column chromatography using isohexane-50% ethyl acetate as eluent to give the product as a pale yellow solid (1.34 g, 67%), NMR δ (CDCl$_3$) 1.31 (t, 3H), 3.84 (s, 3H), 4.32 (q, 2H), 7.0 (d, 1H), 7.22 (d, 1H), 7.39 (d, 1H), 12.2 (bs, 1H);

(iii) Ethyl-N-(3,4-dichlorobenzyl)-4-chloro-5-methoxyindole-2-carboxylate

Sodium hydride (60 mg) was added to a solution of ethyl-4-chloro-5-methoxyindole-2-carboxylate (250 mg), 3,4-dichlorobenzylchloride (0.21 ml) and tetrabutylammoniumiodide (3 mg) in DMF at ambient temperature under an inert atmosphere. The reaction was stirred at ambient temperature for 18 hours then partitioned between ethylacetate (30 ml) and water(30 ml). The organic phase was dried (MgSO4), concentrated under vacuo and the residue purified by column chromatography using isohexane-15% ethylacetate as eluent to yield the product as a white solid (196 mg,48%) NMR: δ (CDCl3) 1.39 (t, 3H), 3.93 (s, 3H), 4.32 (q, 2H), 5.73(s, 2H), 6.84 (dd, iH), 7.06–7.16 (m, 3H), 7.31 (d, 1H), 7.42 (s, 1H)

(iv) Ethyl N-(3,4-dichlorobenzyl)-4-chloro-5-hydroxyindole-2-carboxylate

Trimethylsilyliodide (0.6 ml) was added to a solution of ethyl-N-(3,4-dichlorobenzyl)-4-chloro-5-methoxyindole-2-carboxylate (190 mg) in chloroform (20 ml). The mixture was heated to 50 C. for 18 hours then poured into methanol (50 ml) and concentrated under vacuo. The residue was purified by column chromatography using isohexane-20% ethyl acetate/isohexane as eluent to yield the product as a yellow solid (100 mg,71%) NMR: δ (CDCl3) 1.39 (t, 3H), 4.35 (q, 2H), 5.72 (s, 2H), 6.84 (dd, 1H), 7.05–7.13 (m, 3H) 7.3 (d, 1H) 7.35 (s, 1H);m/z396.2/398.2 (M–H$^+$)

EXAMPLE 15

N-(3,4-Dichlorobenzyl)-2-trifluromethylsulfonoamido-5-hydroxyindole

Sodium methoxide (21 mg) was added to a stirred solution of N-(3,4-dichlorobenzyl)-2-trifluromethylsulfonoamido-5-acetoxyindole (90 mg) in methanol (10 ml). Reaction stirred at ambient temperature for 1.5 hours then concentrated and acidified by the addition of aqueous hydrochloric acid (2M, 5 ml), extracted with dichloromethane and concentrated in vacuo to give brown oil. (50 mg). NMR: δ 5.8 (s, 2H), 6.7 (dd, 1H), 6.9(m, 1H), 7.0(dd, 1H), 7.2 (dd, 1H), 7.3 (m,1H), 7.5 (d, 1H); m/z 465, 467(M–H+).

The starting material for the above was prepared by:

(i) N-(3,4-Dichlorobenzyl)-5-acetoxyindole-2-carboxylic acid

Dimethylaminopyridine (100 mg) and acetic anhydride (1.12 ml) were added to a solution of N-(3,4-Dichlorobenzyl)-5-hydroxyindole-2-carboxylic acid in ethyl acetate (50 ml) and stirred at ambient temperature for 1 hour. Ethanol (10 ml) was added and the reaction was stirred for 30 min. Solvent partially evaporated and iso-hexane added to give a precipitate, which was filtered off and dried to give the product as a white solid (1.2 g). NMR: δ 2.25 (s, 3H), 5.85 (s, 2H), 6.9 (dd, 1H), 7.3–7.6 (m, 5H); m/z 376, 378 (M–H$^+$)

(ii) N-(3,4-Dichlorobenzyl)-2-trifluromethylsufonoamido-5-acetoxyindole

To a stirred solution of N-(3,4-Dichlorobenzyl)-5-acetoxyindole-2-carboxylic acid in DMF (5 ml), under an inert atmosphere, was added HATU (0.27 g), DIPEA (0.12 ml) and trifuromethylsufonamide (97 mg). Reaction was stirred at ambient temperature for 18 hours. The mixture was poured into saturated sodium bicarbonate solution and the resulting precipitate was filtered off and dried to give product. (90 mg). NMR: δ 2.25 (s, 3H), 5.9 (s, 2H), 6.9 (dd, 1H), 7.0(dd, 1H), 7.1(s,1H), 7.35 (m,1H); m/z 506, 508(M–H$^-$)

EXAMPLE 16

N-(3,4-Dichlorobenzyl)-5-hydroxyindole-2-tetrazole

Ammonium chloride (54 mg) and sodium azide (65 mg) were added to a stirred solution of N-(3,4-Dichlorobenzyl)-5-acetoxyindole-2-nitrile in DMF (5 ml). The reaction mixture was heated to 100° C. for 10 hours. A further amount of ammonium chloride (35 mg) and sodium azide (42 mg) was added and the reaction heated to 100° C. for 18 hours. The reaction mixture was acidified by the addition of aqueous hydrochloric acid (2M, 10 ml) and extracted with ethyl acetate, dried, concentrated in vacuo and purified by column chromatography using 20% ethyl acetate in isohexane, increasing to 5% methanol in ethyl acetate to give the product as a brown oil (40 mg) which solidified on standing. NMR: δ 5.9 (s, 2H), 6.75 (dd, 1H), 6.9 (dd, 1H), 7.1(s,1H), 7.1–7.3 (m,2H), 7.5 (d, 1H), 9.0 (s,1H); m/z 360/362 (MH$^+$)

The starting material was prepared by

Methane sulfonyl chloride (0.5 ml) was added to a cooled (0° C.) solution of N-(3,4-dichlorobenzyl)-5-acetoxyindole-2-carboxylic acid (1.12 g) in pyridine (30 ml) and stirred at 0° C. for 1.5 hours. Gaseous ammonia was bubbled through the reaction mixture for 15 min, then excess ammonia removed in vacuo. Reaction mixture cooled to 0° C. and methyl sulfonylchloride (2.5 ml) added to the stirred solution and allowed to reach ambient temperature over 18 hours. Methane sulfonyl chloride (2 ml) added and reaction mixture left to stand for 60 hours. The solvent was removed in vacuo, re-dissolved in dichloromethane and washed 3 times with a 1:1 mixture of aqueous hydrochloric acid (1M) and saturated ammonium chloride solution. The organic extracts were dried concentrated in vacuo and the residue purified by column chromatography, using 10–25% ethyl acetate/iso-hexane to give the desired product. (300 mg). NMR: δ 2.25 (s, 3H), 5.6 (s, 2H), 7.0 (dd, 1H), 7.45–7.65 (m, 4H), 7.7 (d, 1H).

EXAMPLE 17

N-(3,4-dichlorophenylsulphonyl)-5-hydroxyindole-2-carboxylic acid

A solution of anhydrous lithium iodide (870 mg) and methyl_N-(3,4-dichlorophenylsulphonyl)-5-hydroxyindole-2-carboxylate (260 mg) in pyridine (15 ml) was stirred at reflux for 4 hours. The reaction was cooled and concentrated in vacuo. The residue was dissolved in water (20 ml) and acidified with acetic acid. The product was extracted with ethyl acetate and the combined extracts were dried, concentrated in vacuo and the residue purified by column chromatography using dichloromethane-50% ethyl acetate containing 1% acetic acid as eluent to give the desired product as a glass (72 mg, 29%). NMR: δ 6.9 (m, 2H), 7.25 (s, 1H), 7.85 (d, 1H), 7.9 (m, 2H), 8.15 (s, 1H), 9.5 (s, 1H); m/z 385.8 (M−H⁻). The starting material was prepared by (i) Methyl N-(3,4-dichlorophenylsulphonyl)-5-benzyloxyindole-2-carboxylate Sodium Hydride (60% dispersion, 444 mg) was added to a stirred solution of methyl 5-benzyloxyindole-2-carboxylate (2.08 g) in DMF (50 ml) at room temperature. After 1 hour, 3,4-dichlorobenzenesulphonyl chloride (2.72 g) was added. Stirring was continued for 2 hours after which the reaction mixture was partitioned between water and ethyl acetate. Combined organic extracts were dried and concentrated in vacuo and the residue purified by column chromatography using isohexane-20% ethyl acetate as eluent to give the desired product as a white solid (2.02 g, 56%). NMR: δ3.85 (s, 3H), 5.1 (s, 2H), 7.2 (m, 1H), 7.4 (m, 7H), 7.9 (s, 2H), 8.0 (d, 1H), 8.2 (s, 1H); m/z 489.8 (MH⁺).

(ii) Methyl N-(3,4-dichlorophenylsulphonyl)-5-hydroxyindole-2-carboxylate

A suspension of 5% palladium on carbon in ethyl acetate (450 ml) and methyl N-(3,4-dichlorophenylsulphonyl)-5-benzyloxyindole-2-carboxylate(2.01 g) was stirred at 60° c under hydrogen at atmospheric pressure for 48 hours. The catalyst was removed by filtration and the filtrate concentrated in vacuo. The residue was purified by column chromatography using 20%ethyl acetate/isohexane as eluent to give the desired product as a gum (270 mg,16%). NMR: δ 3.85(s, 31H), 7.0 (m, 2H), 7.35 (s, 1H), 7.9 (m, 3H), 8.1 (s, 1H), 9.6 (s, 1H); m/z 401.9 (MH⁺).

EXAMPLE 18

N-(3,4-Dichlorobenzyl)-5-acetoxyindole-2-carboxylic acid

To a solution of N-(3,4-Dichlorobenzyl)-5-hydroxyindole-2-carboxylic acid (10 g) in warm ethyl acetate (250 ml) was added 4-dimethylaminopyridine (100 mg) and acetic anhydride (5.0 ml) and the resulting mixture was stirred for 2 hours. The organics were washed with 1N HCl and dried. Hexane was added to cause crystallision of the product. The solid was filtered and washed with hexane to give the desired product. (5 g, 44%). ¹H NMR (DMSO-d₆) δ 2.25 (s, 3H), 5.85 (s, 2H), 6.9 (dd, 1H), 7.05 (dd, 1H), 7.3–7.6 (m, 5H); m/z 378, 380 (MH⁺).

EXAMPLE 19

Pharmaceutical Compositions

This Example illustrates, but is not intended to limit, representative pharmaceutical dosage forms of the invention as defined herein (the active ingredient being termed "Compound X"), for therapeutic or prophylactic use in humans:

Example A

| (a) Tablet I | mg/tablet |
| --- | --- |
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
| --- | --- |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
| --- | --- |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
| --- | --- |
| Compound X | 10 |
| Lactose Ph.Eur | 488.5 |
| Magnesium | 1.5 |

| (e) Injection I | (50 mg/ml) |
| --- | --- |
| Compound X | 5.0% w/v |
| 0.1M Sodium hydroxide solution | 15.0% v/v |
| 0.1M Hydrochloric acid | to adjust pH to 7.6 |
| Polyethylene glycol 400 | 4.5% w/v |
| Water for injection | to 100% |

27
-continued

| (f) Injection II | (10 mg/ml) |
|---|---|
| Compound X | 1.0% w/v |
| Sodium phosphate BP | 3.6% w/v |
| 0.1M Sodium hydroxide solution | 15.0% w/v |
| Water for injection | to 100% |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note:
Compound X in the above formulations may comprise a compound as illustrated in Examples 1 to 3 herein.

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglyccrol oleate or oleic acid.

28

What is claimed is:
1. A compound of the formula (I):

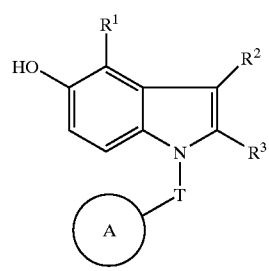

wherein:

$R^1$ is hydrogen, halo or methoxy;

$R^2$ is hydrogen, halo, methyl, ethyl or methoxy;

$R^3$ is carboxy, tetrazolyl or —CONHSO$_2$R$^4$ where $R^4$ is methyl, ethyl, phenyl, 2,5-dimethylisoxazolyl or trifluoromethyl;

T is —CH$_2$— or —SO$_2$—; and ring A is 3-chlorophenyl, 4-chlorophenyl, 3-trifluoromethylphenyl, 3,4-dichlorophenyl, 3,4-difluorophenyl, 3-fluoro-4-chlorophenyl, 3-chloro-4-fluorophenyl or 2,3-dichloropyrid-5-yl;

or a pharmaceutically acceptable salt or prodrug thereof.

2. A compound according to claim 1 wherein ring A is 3-chlorophenyl, 4-chlorophenyl, 3-trifluoromethylphenyl, 3,4-dichlorophenyl, 3,4-difluorophenyl, 3-fluoro-4-chlorophenyl or 3-chloro-4-fluorophenyl.

3. A compound according to claim 2 wherein ring A is 3,4-dichlorophenyl, 3-fluoro-4-chlorophenyl or 3-chloro-4-fluorophenyl.

4. A compound according to claim 1 wherein ring A is 3,4-dichlorophenyl, 2,3-dichloropyrid-5-yl or 3-chloro-4-fluorophenyl.

5. A compound according to claim 1 wherein T is —CH$_2$—.

6. A compound according to claim 1 where $R^3$ is carboxy.

7. A compound according to claim 1 wherein in the compound of formula (I), $R^1$ is hydrogen;

$R^2$ is hydrogen;

$R^3$ is carboxy;

T is —CH$_2$—; and ring A is 3,4-dichlorophenyl or 3-chloro-4-fluorophenyl;

or a pharmaceutically acceptable salt or prodrug thereof.

8. A process for preparing a compound according to claim 1 which process comprises:

a) reacting a compound of formula (II):

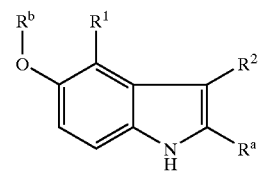

where $R^a$ is a group $R^3$ as defined in claim 1 or protected form of a group $R^3$, $R^b$ is hydrogen or a hydroxy protecting group, and $R^1$ and $R^2$ are as defined in claim 1, with a compound of formula (III):

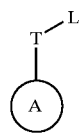
(III)
where T and ring A are as defined in claim 1, and L is a displaceable group; and thereafter optionally;
i) removing any protecting groups; and/or
ii) forming a pharmaceutically acceptable salt or prodrug thereof.
9. A pharmaceutical composition comprising a compound according to any one of claims 1 to 7 in combination with a pharmaceutically acceptable carrier.
* * * * *